United States Patent [19]

Cahill, Jr. et al.

[11] Patent Number: 4,709,058

[45] Date of Patent: Nov. 24, 1987

[54] PROCESS FOR THE PRODUCTION OF MACROCYCLIC ESTERS BY THE DEPOLYMERIZATION OF POLYESTERS

[75] Inventors: Joseph Cahill, Jr., Fort Mitchell, Ky.; Herbert G. Rodenberg, Cincinnati, Ohio

[73] Assignee: National Distillers and Chemical Corporation, New York, N.Y.

[21] Appl. No.: 909,760

[22] Filed: Sep. 19, 1986

[51] Int. Cl.⁴ .................. C07D 323/00; C07D 313/00; C07D 327/00; C07D 327/02

[52] U.S. Cl. ...................................... 549/267; 549/10; 549/11; 549/266

[58] Field of Search .................... 549/267, 266, 10, 11

Primary Examiner—Norma S. Milestone
Attorney, Agent, or Firm—Kenneth D. Tremain; Gerald A. Baracka

[57] ABSTRACT

The catalytic thermal depolymerization of polyesters to produce macrocyclic esters suitable for fragrance applications is carried out using an olefin polymer. High yields of the corresponding macrocyclic ester are produced at high rates while substantially eliminating reactor fouling and the formation of undesirable by-products. The depolymerization is most advantageously conducted using polyethylene.

14 Claims, No Drawings

PROCESS FOR THE PRODUCTION OF MACROCYCLIC ESTERS BY THE DEPOLYMERIZATION OF POLYESTERS

BACKGROUND OF THE INVENTION

1. Field of the Invention:

Macrocyclic esters are obtained by the thermal depolymerization of the corresponding linear polyesters accompanied by ring closure. For such processes, the polyester is heated at an elevated temperature in the presence of a catalyst and the macrocyclic compound formed during the course of the depolymerization is removed from the reaction zone.

2. Description of the Prior Art:

Chlorides, nitrates, carbonates and oxides of magnesium, manganese, iron, cobalt and tin (all in the divalent state) are employed for the depolymerization of linear polyesters in the process of U.S. Pat. No. 2,092,031. In the process of U.S. Pat. No. 4,165,321 Lewis metal salts such as the oxides, hydroxides, halides or carboxylates of Group IIIa, IVa, IVb, Va, VIIb and VIII metals are disclosed to be useful catalysts. Yasakawa et. al. reported the use of lead catalysts (oxide, hydroxide, carbonate, nitrate, borate or organic acid salts) for the preparation of large ring lactones via thermal depolymerization in Chemical Abstracts, Vol. 78 (1973), 158966q and 158968s. Cyclic esters are also obtained via thermal degradation of polyesters using $SnCl_2.2H_2O$ in Chemical Abstracts, Vol. 86 (1977), 156163s. In U.S. Pat. Nos. 4,105,672, 4,136,098, and 4,157,330 tin carboxylates and organotin compounds are employed in conjunction with dialkyl-(3,5-di-t-butyl-4-hydroxybenzyl) phosphates to catalyze the reaction. In British patent No. 1,108,720 the formation of cyclic ester anhydrides of alpha-hydroxycarboxylic acids in vacuo by depolymerizing the corresponding linear polymer at 200°-240° C. in the presence of lead (II) stearate is described.

In view of the problems associated with the use of heavy metal catalysts, aluminum oxide has been used to catalyze depolymerizations carried out at atmospheric pressure using superheated steam in Czech patent No. 108,762. The use of metallic aluminum was also reported for the thermal depolymerization of polyesters to form cyclic esters and lactones in Japanese patent No. 36-1375 (1961). Aluminum alcoholates are disclosed for the preparation of large-ring lactones in Japanese patent publication No. 72 25,071.

Mixed-metal catalysts having a carbonic acid radical and based on aluminum and sodium, wherein aluminum is the predominant metal, are also disclosed for the depolymerization of polyesters to produce macrocyclic compounds in Japanese patent disclosure Nos. 1979-103,884 (appln. No. 1978-8,809); 1979-115,390 (appln. No. 1978-22,023); and 1980-120,581 (appln. No. 1979-26,741). The mixed-metal catalysts of these Japanese references all have aluminum:sodium weight ratios greater than about 3.5:1. The catalysts are typically prepared by treating an aqueous mixture of aluminum hydroxide and caustic soda with carbon dioxide. Mixed-metal catalysts comprised of aluminum alkoxides or aluminum carboxylates with an alkali metal or magnesium alkoxide or carboxylate are utilized in the process of U.S. Pat. Nos. 4,393,223 and 4,499,288. Dawsonite, a naturally occurring basic carbonate of sodium and aluminum, is also disclosed as an effective catalyst for the thermal depolymerization (see U.S. Pat. No. 4,594,434).

A problem common to all of the above-described catalytic thermal depolymerization processes is the viscosity of the reaction mass. As the depolymerization proceeds, the viscosity of the reaction mixture increases due to chain-growth reactions occurring between partially depolymerized fragments and an intractable plastic mass is formed. Stirring becomes extremely difficult and, in some cases, impossible. Mixing is non-existent or, at the very best, highly inefficient. Thus, heat transfer within the highly viscous reaction mass is very poor and localized "hot spots" occur resulting in charring of the reaction mixture and reactor fouling. As a result of these viscosity/heat transfer problems, reaction times are extended, yields are reduced, and undesirable malodorous decomposition products are obtained.

In an effort to overcome these problems, processes have been developed whereby specialized mixing equipment is employed and/or the reaction is conducted in the presence of other compounds. U.S. Pat. Nos. 4,165,321 and 4,218,379, for example, describe processes wherein the reaction is carried out in the presence of a monocarboxylate moiety derived from an aliphatic or aromatic monocarboxylate and wherein agitation is employed which provides top-to-bottom mixing throughout essentially the total volume of the reaction mass in an inverted multiple-blade conical vessel wherein the blades have a helical configuration and are arranged to rotate throughout essentially the entire reaction mass and in close proximity to the interior surface of said conical vessel and in a direction which provides a downward flow within the reaction mixture.

In Japanese patent disclosure No. 1980-120,581 (appln. No. 1979-26,741) the depolymerization and ring formation are carried out in the presence of at least one compound selected from the group consisting of polyoxyalkylene glycols, polyoxyalkylene glycol esters, polyoxyalkylene glycol ethers, monobasic acids, monobasic acid esters, monobasic anhydrides, monovalent alcohols and monovalent alcohol esters. A process is disclosed in Japanese patent No. 73-1972 wherein the depolymerization is carried out in the presence of a paraffin oil. Whereas such processes overcome some of the viscosity/heat transfer problems associated with the reaction, undesirable decomposition products which have objectionable odors result. Such processes are therefore not suitable for the production of macrocyclic compounds intended for critical fragrance applications.

It would be highly desirable therefore if a process were available whereby the viscosity/heat transfer problems associated with these depolymerization reactions were avoided and the formation of undesirable malodorous by-products was minimized or completely eliminated.

SUMMARY OF THE INVENTION

We have now quite unexpectedly discovered that the depolymerization can be advantageously carried out in an olefin polymer. In addition to significantly reducing the viscosity of the reaction mass and thus eliminating problems associated with mixing and heat transfer, other advantages are realized with the present improved process. High yields of the corresponding macrocyclic product are produced at high rates while substantially eliminating reactor fouling and the formation of undesirable malodorous by-products.

For the present improved process, a polyester is heated at a temperature in the range 200° C. to 400° C. and pressure less than about 50 mm Hg in the presence of from 0.01 to 10 weight percent catalyst, based on the polyester, and in the presence of an inert olefin polymer which is a liquid under the operating conditions. The weight ratio of olefin polymer to polyester can range from 100:1 to 1:20. Polyethylene is an especially useful medium for the reaction. Most generally, the depolymerization is carried out at a temperature from 275° C. to 350° C. and pressure from about 10 mm Hg to 0.01 mm Hg using from 0.1 to 5 weight percent catalyst. The process is particularly advantageous for continuous or semi-continuous operation wherein the polyester is continually or incrementally fed to the reactor while continuously removing the macrocyclic ester product. Macrocyclic esters having from 8 to 20 carbon atoms essentially free of undesirable malodors are conveniently obtained by the process of this invention.

DETAILED DESCRIPTION

The present invention relates to an improved process for the depolymerization of linear polyesters accompanied by ring closure to form macrocyclic compounds having from 8 to 20 atoms in the ring. Polyesters employed for the process are obtained by conventional methods known to the art and are derived from conventional dicarboxylic acids, diols and hydroxymonocarboxylic acids. Dicarboxylic acids employed are preferably aliphatic and may be saturated or contain olefinic unsaturation and can be branched or straight-chain. Polyesters derived from aromatic or alicyclic dicarboxylic acids can also be employed, however.

The aliphatic dicarboxylic acids will typically contain from 3 up to about 18 carbon atoms and, more preferably, from about 8 to 14 carbon atoms. Especially useful dicarboxylic acids include, for example, malonic acid, maleic acid, succinic acid, glutaric acid, adipic acid, pimelic acid, azelaic acid, sebacic acid, undecanedioic acid, dodecanedioic acid, brassylic acid, pentadecanedioic acid, and the like. Mixtures of two or more dicarboxylic acids may also be employed. Polyesters derived from $C_{9-13}$ saturated aliphatic dicarboxylic acids are especially preferred since macrocyclic compounds produced therefrom exhibit especially desirable fragrance properties and are useful in a wide variety of cosmetic applications.

Diols from which the polyesters are derived are primarily aliphatic diols having from 2 to 12, and more preferably, 2 to 6 carbon atoms. The diols are preferably saturated and can be either straight-chain or branched. Useful diols include ethylene glycol, 1,2- or 1,3-propanediol, 1,2-, 1,3-, or 1,4-butanediol, 1,6-hexanediol, 3-methyl-1,5-pentanediol, 2,3-dimethyl-2,3-butanediol, 1,8-octanediol, 2-ethylhexanediol, 1,10-decanediol, 1,12-dodecanediol, diethylene glycol, triethylene glycol, and the like. Alicyclic diols such as 1,4-cyclohexadimethanol may also be employed. Polyesters derived from ethylene glycol and di-, tri- and tetraethylene glycol are especially advantageous.

Hydroxymonocarboxylic acids from which useful polyesters can be derived include 15-hydroxypentadecanoic acid, 16-hydroxyhexadecanoic acid, 10-oxa-16-hydroxyhexadecanoic acid, 11-oxa-16-hydroxyhexadecanoic acid, 12-oxa-16-hydroxyhexadecanoic acid, 10-thia-16-hydroxyhexadecanoic acid, 11-thia-16-hydroxyhexadecanoic acid, 12-thia-16-hydroxyhexadecanoic acid, and the like.

It is particularly advantageous if the polyesters are terminated with monocarboxylic acid(s) and/or monofunctional alcohol(s) to control the molecular weight and viscosity of the polymer. Polyesters having acid values and hydroxyl values less than about 20 and, more usually, less than 10 are particularly useful. The degree of polymerization of the polyesters will generally be between about 5 and 150 but can be higher, if desired.

Employing polyesters of the above types, it is possible to obtain macrocyclic compounds having from 8 to 20 carbon atoms in the ring. The macrocyclic compounds will conform to the general formulae:

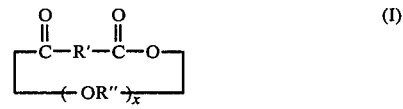

where R' is a bivalent aliphatic hydrocarbon radical, which can be branched or straight chain, saturated or contain unsaturation, having from 1 to 16 carbon atoms, R" is a saturated bivalent aliphatic hydrocarbon radical having 2 to 12 carbon atoms and x is an integer from 1 to 4;

where R''' is a bivalent aliphatic hydrocarbon radical having from 6 to 18 carbon atoms; or

where R", R''' and x are the same as defined above and A is oxygen or sulfur.

Especially useful macrocyclic compounds of the type (I) are those wherein the moiety R' is a saturated aliphatic radical having from 6 to 12 carbon atoms, the aliphatic radical R" has 2 to 6 carbon atoms, and x is 1 or 2. Preferred macrocyclic products of the types (II) and (III) are those wherein R''' is a saturated bivalent aliphatic hydrocarbon radical having from 10 to 14 carbon atoms, the aliphatic radical R" contains from 2 to 6 carbon atoms, A is oxygen, and x is 1 or 2.

Illustrative macrocyclic products which can be conveniently produced by the depolymerization process of this invention include: 3,6,9-tridecamethylene malonate, dodecamethylene malonate, decamethylene malonate, ethylene suberate, ethylene azelate, 3-oxa-pentamethylene azelate, 3-methylpentamethylene sebacate, ethylene undecanedioate, ethylene dodecanedioate, ethylene brassylate, ethylene-alpha-methylbrassylate, ethylene-alpha,alpha-dimethylbrassylate, ethylene-alpha-ethylbrassylate, pentadecanolide, 12-oxa-pentadecanolide, 12-thia-pentadecanolide, hexadecanolide, 10-oxa-hexadecanolide, 11-oxa-hexadecanolide, 11-thia-hexadecanolide, 12-oxa-hexadecanolide and the like. The process of this invention is particularly advantageous for the preparation of ethylene brassylate and ethylene dodecanedioate by the depolymerization of polyethylene brassylate and polyethylene dodecanedioate, respectively.

The macrocyclic products are primarily useful in cosmetic applications. They impart desirable fragrance properties and/or enhance the fragrance characteristics of other compounds combined therewith. For example, they can be used in detergents (heavy duty and regular laundry), soaps (bar soaps, dish soaps and specialty beauty soaps), personal care products (bath oils, shampoos, hair rinses, deodorants, shaving creams and mouthwashes), and as fine fragrance components for perfumes, perfume oils, perfume fixatives, colognes, aftershave lotions and the like.

The present improved process is conducted in an olefin polymer in accordance with conventional procedures known to the art. Details of thermal depolymerizations are well known and in this regard reference may be had to the prior art previously mentioned. The reaction is typically conducted at a temperature in the range 200° C. to 400° C. and, more usually, from 275° C. to 350° C. Subatmospheric pressures are employed to facilitate removal of the macrocyclic product formed. Pressures less than about 50 mm Hg and, more preferably, in the range 0.1 mm Hg to 10 mm Hg are generally employed. A metal catalyst is employed in an amount from 0.01 to 10 weight percent and, more preferably, from 0.1 to 5 weight percent based on the weight of the polyester.

Metal catalysts which can be used include compounds of Group IIa, IIIa, IVa, IVb, Va, VIb, VIIb, and VIII metals (Periodic Table of the Elements, Handbook of Chemistry and Physics, 65th Ed., CRC Press), particularly oxides, hydroxides, halides, and carboxylates of these metals. Oxides, hydroxides, chlorides, and carboxylates of organic acids having from 2 to 20 carbon atoms of magnesium, aluminum, titanium, manganese, iron, cobalt, tin, and lead are particularly useful. Illustrative catalysts of the above types which can be utilized for the depolymerization include but are not limited to aluminum oxide, lead (II) oxide, red lead, lead (II) oxalate, lead (II) stearate, lead (II) palmitate, lead (II) coconoates, cobalt (II) chloride, tin (II) oxide, tin (IV) oxide, tin (II) chloride, tin (II) oxalate, tin (II) stearate, iron (III) chloride, antimony (II) chloride, magnesium oxide, magnesium chloride hexahydrate, manganese (II) chloride tetrahydrate, cobalt (II) chloride hexahydrate, iron (II) chloride tetrahydrate, n-butyl stannoic acid, di-n-butyl tin diacetate, condensed butyl titanate, and the like.

Mixed metal catalysts wherein aluminum is present with an alkali metal or magnesium are particularly effective and especially useful in the present process. Such mixed metal catalysts are disclosed in U.S. Pat. Nos. 4,393,223, 4,499,288, and 4,594,434, details of which are incorporated herein by reference.

For the improved process of this invention, the depolymerization reaction is carried out in an inert olefin polymer which is a liquid under the prevailing operating conditions. Furthermore, the vapor pressure of the polyolefin should be greater than the total pressure of its surroundings, i.e., it should not boil under the operating conditions. This facilitates removal of the macrocyclic ester product formed during the reaction and insures that the product is substantially pure.

Olefin polymers employed for this purpose can be derived from $C_{2-8}$ olefins or mixtures thereof. Ethylene homopolymers and copolymers wherein ethylene is the predominant monomer are particularly useful for the process. Polyethylene is particularly advantageous. The weight ratio of the polyolefin to polyester can range from 100:1 to 1:20. In a particularly useful embodiment of the invention, the weight ratio of polyolefin to polyester is in the range 20:1 to 1:12.

The temperature, pressure, amount of catalyst, and ratio of polyolefin to polyester can vary depending on the materials employed, the design of the process equipment, and the method of operation. Whereas the process can be carried out as a batch operation wherein all of the materials are charged to the reactor at the outset, maximum benefit is realized when the depolymerization is conducted on a continuous or semi-continuous basis. With such manner of operation, the polyester is continuously or incrementally fed to the reactor containing all or a major portion of the polyolefin while continuously removing the macrocyclic ester product which is formed. All of the catalyst may be present in the reactor with the polyolefin or all or a portion of the catalyst may be combined with the polyester and fed to the reactor in this manner. Catalyst may also be separately fed to the reactor or metered in solution with the polyolefin, which can be either fresh or recycled polyolefin.

High yields of macrocyclic ester are readily obtained with the improved process of the present invention. The process has the further advantage that the macrocyclic esters thus produced are high quality products, i.e., they are substantially free of undesirable malodorous by-products and catalyst residue, and are readily distilled to yield highly desirable fragrance products suitable for use in the most critical fragrance applications. Moreover, a manageable viscosity is maintained throughout the course of the reaction. This reduces wear and tear on the process equipment (seals, motor, etc.), reduces energy consumption, and permits the reaction to be carried out on a scale larger than was heretofore possible. A further advantage of the present process is the fact that reactor fouling is minimized since the residues formed during the course of the depolymerization remain dispersed within the reaction mixture and do not adhere to the walls of the reactor, stirrer blades, etc. Furthermore, insoluble dispersed residues are removed from the reactor when the polyolefin is discharged. This latter feature is particularly advantageous for continuous operation since, by continuously removing a portion of the polyolefin from the reactor, residues formed during the depolymerization reaction are also removed and prevented from building up within the reactor. Residue buildup within the reactor has heretofore been a problem with depolymerization processes and has prevented true continuous operation. If desired, the residues can be removed from the polyolefin by filtering, decanting, centrifuging, etc. and the polyolefin recycled for further use in the process.

These and other advantages are evident from the following illustrative examples. In these examples all parts and percentages are on a weight basis unless otherwise indicated. The polyethylene brassylate used in the examples was prepared by charging a top-agitated resin kettle fitted with a distillation head and condenser with 109 parts dimethyl brassylate and 30.5 parts polymer grade ethylene glycol. About 2.3 percent methyl esters of a mixture of $C_{16-22}$ fatty acids, based on the dimethyl brassylate, was included as a chain terminator. A supported titanium catalyst (0.08 part), prepared from tetraisopropyl titanate and a naturally acidic montmorillonite clay in accordance with the teaching of U.S. Pat. No. 4,032,550, was then added to the reaction mixture under a positive pressure of nitrogen and heating begun. When the temperature of the reaction mixture reached about 180° C. methanol began distilling from the reaction mixture and was collected. After most of the methanol was removed and the temperature increased to about 195° C.–205° C., a vacuum of 2 in Hg was applied and increased slowly to 30 in Hg. Samples were periodically removed from the reactor for analysis and after about 11 hours, when the mixture had an acid value of 0.1 and hydroxyl value of 15.3, heating was terminated. The reaction mixture was cooled to about 180° C. and the vacuum broken with nitrogen. The high molecular weight polyethylene brassylate, viscosity 117 centistokes at 210° C., was filtered to remove the supported titanium catalyst. 2.72 Weight percent of a mixed potassium-aluminum salt KAl $(OC_2H_4OC_2H_4OC_2H_5)_3(OOC_{18}H_{35})$ was dissolved in the polyester for use in the depolymerization of the subsequent reactions. A polyester feed based on polyethylene dodecanedioate containing the potassium-aluminum salt at a 2.72 weight percent level was obtained following the above procedure. Similar polyester feeds containing lead stearate and a synthetic Dawsonite obtained in accordance with the process of U.S. Pat. No. 4,238,458 as the depolymerization catalysts were also prepared.

EXAMPLE I

Ethylene brassylate was prepared by depolymerizing the polyethylene brassylate containing the mixed potassium-aluminum salt at a 2.72 weight percent level. The reaction was conducted in polyethylene (1:1 wt. ratio of polyethylene to polyester). For the depolymerization, 70 grams of the polyester was charged to a glass reaction vessel containing 70 grams polyethylene homopolymer (A-C ® 617 manufactured by Allied Corporation). The reactor was equipped with a stirrer, thermometer, and short-path adapter connected to a receiving flask with a condenser. The mixture was heated under reduced pressure with agitation to about 250° C. at which point distillate began to collect. Reaction was continued while maintaining the pressure between 0.15 mm Hg and 0.22 mm Hg up to a maximum temperature of 336° C. There was no noticeable thickening of the reaction mixture. Heating was terminated after about 4½ hours when the distillation rate of ethylene brassylate slowed. 58.4 Grams crude product (83.4% yield) essentially free of malodorous materials and which was readily distilled to obtain a high quality fragrance grade ethylene brassylate was recovered.

To demonstrate the ability to reuse the polyethylene and to operate on a semi-continuous basis, a second 70 gram charge of the polyethylene brassylate feed containing the mixed potassium-aluminum catalyst was made to the reactor after it had been allowed to cool somewhat. Heating was then resumed (pressure 0.11–0.25 mm Hg; temperature max. 331° C.) and 61.3 grams (87.5% yield) ethylene brassylate recovered in approximately 3 hours. Still another 70 gram polyester charge was made to the reactor and 56.0 grams (80% yield) ethylene brassylate recovered from this run after only 79 minutes reaction time. There was no observable difference in the manner in which either of the subsequent reactions proceeded and the recovered product from both of these runs was comparable in quality to that obtained from the first reaction. Similar results were obtained using the polyethylene brassylate containing the Dawsonite catalyst.

EXAMPLES II–IV

Following the general procedure described above, additional depolymerizations were carried out in accordance with the process of this invention using different polyolefin:polyester ratios. The polyethylene (PE) and polyethylene brassylate (PEB) used were the same as employed for Example I. PE:PEB ratios ranged from 2:1 to 9.3:1. Details of the reactions and yields obtained are set forth in Table I. Additional incremental additions of polyester were made as indicated. The yield reported in the table is based on the total amount of polyethylene brassylate charged and total amount of ethylene brassylate recovered for all of the runs for each example.

EXAMPLE V

Following the procedure of Example I, polyethylene dodecanedioate was depolymerized to obtain ethylene dodecanedioate. For the reaction, 75 grams polyethylene dodecanedioate containing 2.72 weight percent of the potassium-aluminum salt and 150 grams polyethylene homopolymer were charged to the reactor and the mixture heated to a maximum temperature of 348° C. at a pressure ranging from 1.1 mm Hg to 1.3 mm Hg. 89.7% Yield ethylene dodecanedioate was recovered in approximately 1½ hours. There was no noticeable increase in the viscosity of the reaction mixture throughout the course of the reaction. Three additional 75 gram increments of the polyethylene dodecanedioate were charged at approximately 1½ hour intervals. The total yield of ethylene dodecanedioate obtained was 92.0 percent. The ethylene dodecanedioate was essentially free of malodorous materials and, upon distillation, yielded a high purity product useful for fragrance applications. Inspection of the interior reactor walls and agitator shaft and blades showed them to be virtually residue-free at the conclusion of these runs. Comparable results were obtained using a polyester feed containing lead stearate as the depolymerization catalyst.

When the polyethylene was replaced with polyethylene glycol having an average molecular weight of 3350, undesirable highly colored and malodorous by-products were produced. Similarly, attempts to substitute polyvinyl acetate and oxidized ethylene homopolymer (acid number 30) for the polyethylene were

TABLE I

| Example No. (Run No.) | Charge (Grams) PE | Charge (Grams) PEB | Pressure (mm Hg) | Maximum Temperature (°C.) | Reaction Time (Min.) | Ethylene Brassylate (Grams) | Total Percent Yield |
|---|---|---|---|---|---|---|---|
| II(1) | 600 | 300 | 1.1–2.0 | 340 | 180 | 245 | — |
| II(2) | — | 296 | 0.9–1.9 | 347 | 180 | 303 | 91.9 |
| III(1) | 400 | 51.7 | 0.6–0.9 | 342 | 90 | 43.5 | — |
| III(2) | — | 54.6 | 0.7–0.9 | 341 | 90 | 55.9 | — |
| III(3) | — | 52.7 | 0.9–1.1 | 342 | 90 | 47.1 | 92.1 |
| IV(1) | 125 | 13.4 | 0.22–0.30 | 318 | 163 | 10.4 | — |
| IV(2) | — | 12.5 | 0.16–0.24 | 306 | 178 | 12.5 | 88.4 | unsuccessful. The polyvinyl acetate gave a very low yield (21.9%) of crude distillate and the residue remaining in the reactor was extremely gummy. A low yield (27.1%) was also obtained using the oxidized ethylene homopolymer. The viscosity of the reaction mixture increased throughout the depolymerization and ultimately gelled.

EXAMPLE VI

To demonstrate the ability to carry out the process of this invention on a continuous basis, polyethylene dodecanedioate was depolymerized in polyethylene in accordance with the procedure of U.S. Pat. No. 4,165,321. For the reaction, polyethylene dodecanedioate containing the mixed potassium-aluminum catalyst (2.72 wt. %) maintained at 100° C. with agitation was continuously metered from a stainless steel holding tank into a heated stainless steel inverted vertical cone reactor containing 190 pounds polyethylene homopolymer. The reactor was equipped with two conical helicoidal blades whose axis coincided with the cone axes of the bowl and which intermeshed as they were rotated in opposite directions to provide highly efficient top-to-bottom mixing throughout the total volume of the reaction mixture. The blades were positioned to provide maximum blade-to-wall clearance of about 0.25 inch and were rotated at 20 rpm. A high torque motor was used to drive the blades and the load on the motor was constantly monitored. Temperature of the reaction mixture was maintained in the range 342° C. to 343° C. and the pressure was maintained from 3.0 mm Hg to 5.0 mm Hg. Ethylene dodecanedioate was continuously distilled from the reactor and the rate of addition of polyester adjusted to maintain the proper material balance. Ethylene dodecanedioate was obtained at a rate of 36.8 pounds per hour over a 63-hour period during which time the load on the motor remained at a constant 13 percent of the predetermined maximum load limit. The motor is equipped with an automatic shut off in the event the maximum load limit (100%) is reached. Yield of ethylene dodecanedioate was 90.3 percent. The weight ratio of polyethylene to polyethylene dodecanedioate, calculated for the total reaction period, was 1:12. The insoluble residue formed during the course of the depolymerization was dispersed in the polyethylene and the residue was readily and conveniently removed from the reactor by discharging the dispersion.

For comparative purposes and to demonstrate the significant improved results obtained with the process of this invention, the above reaction was repeated except that the polyethylene was omitted. The rate of distillation of the ethylene dodecanedioate was 30.8 pounds per hour over the period of operation (35 hours) and the total yield of ethylene dodecanedioate was only 73.2 percent. At one point during the reaction the load on the motor reached 50 percent indicating a significant increase in the viscosity of the reaction mixture. At the conclusion of the run after the polyester feed was discontinued, it was necessary to continue heating the reactor for about one hour in order to obtain the residue produced during the depolymerization in acceptable granular form so that it could be discharged from the reactor.

EXAMPLE VII

Employing the general procedure and conditions described for Example VI, ethylene brassylate was continuously produced by the depolymerization of polyethylene brassylate. Ethylene brassylate was obtained at a rate of 30.4 pounds per hour and the yield of ethylene brassylate was 82.1%. The load on the motor remained at a constant 12 percent over the entire period of operation.

A series of nine comparative runs were carried out without the polyethylene. The highest distillation rate obtained was 29.1 pounds per hour and the highest yield was 77.6%. The viscosity developed in all of these runs was significantly higher than obtained with the reaction conducted using the polyethylene. In fact, for six of the nine runs the viscosity became so high that the load limit of the agitator motor was reached, i.e., 100% load, and the motor was automatically shut off.

We claim:

1. An improved thermal depolymerization process for the production of macrocyclic esters having from 8 to 20 carbon atoms of the formula

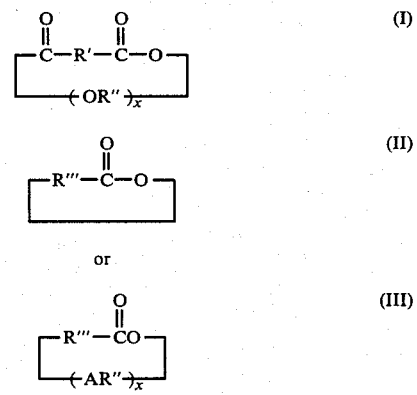

where R' is a bivalent aliphatic hydrocarbon radical having from 1 to 16 carbons, R" is a saturated bivalent aliphatic hydrocarbon radical having from 2 to 12 carbon atoms, R''' is a bivalent aliphatic hydrocarbon radical having from 6 to 18 carbon atoms, x is an integer from 1 to 4, and A is oxygen or sulfur, which comprises heating the corresponding linear polyester and an olefin polymer at a temperature from 200° C. to 400° C. and pressure less than 50 mm Hg in the pressure of 0.01 to 10 weight percent of a metal catalyst, based on the polyester, while removing the macrocyclic ester product, said olefin polymer being inert and liquid under the operating conditions of the process and the weight ratio of said olefin polymer to polyester ranging from 100:1 to 1:20.

2. The process of claim 1 wherein the catalyst is a metal compound or a mixed-metal compound of a metal selected from Group IIa, IIIa, IVa, IVb, Va, VIb, VIIb, and VIII.

3. The process of claim 2 wherein the olefin polymer is an ethylene homopolymer or a copolymer of ethylene having ethylene as the predominant monomer.

4. The process of claim 3 wherein the depolymerization is carried out at a temperature from 275° C. to 350° C. and pressure from 0.1 mm Hg to 10 mm Hg.

5. The process of claim 4 wherein the catalyst is present in an amount from 0.1 to 5 weight percent, based on the weight of the polyester, and the weight ratio of olefin polymer to polyester ranges from 20:1 to 1:12.

6. The process of claim 5 wherein the olefin polymer is polyethylene.

7. The process of claim 6 wherein the catalyst is an oxide, hydroxide, halide, or carboxylate of magnesium, aluminum, titanium, manganese, iron, cobalt, tin or lead.

8. The process of claim 7 wherein the depolymerization is conducted as a continuous or semi-continuous operation.

9. The process of claim 8 wherein the polyester is polyethylene brassylate and the macrocyclic ester is ethylene brassylate.

10. The process of claim 8 wherein the polyester is polyethylene dodecanedioate and the macrocyclic ester is ethylene dodecanedioate.

11. The process of claim 6 wherein the catalyst is a mixed metal compound wherein aluminum is present with an alkali metal or magnesium.

12. The process of claim 11 wherein the depolymerization is conducted as a continuous or semi-continuous operation.

13. The process of claim 12 wherein the polyester is polyethylene brassylate and the macrocyclic ester is ethylene brassylate.

14. The process of claim 12 wherein the polyester is polyethylene dodecanedioate and the macrocyclic ester is ethylene dodecanedioate.

* * * * *